United States Patent
Tsuchida et al.

(10) Patent No.: US 7,247,729 B2
(45) Date of Patent: Jul. 24, 2007

(54) METHOD FOR PRODUCING PIPECOLAMIDE DERIVATIVE

(75) Inventors: Toshio Tsuchida, Yamato (JP); Katsura Kaneko, Yokohama (JP); Naoki Matsumoto, Fujisawa (JP)

(73) Assignee: Mercian Corporation, Tokyo (JP)

( * ) Notice: Subject to any disclaimer, the term of this patent is extended or adjusted under 35 U.S.C. 154(b) by 159 days.

(21) Appl. No.: 10/488,470

(22) PCT Filed: Sep. 10, 2002

(86) PCT No.: PCT/JP02/09200

§ 371 (c)(1),
(2), (4) Date: Oct. 27, 2004

(87) PCT Pub. No.: WO03/024930

PCT Pub. Date: Mar. 27, 2003

(65) Prior Publication Data

US 2005/0065345 A1    Mar. 24, 2005

(30) Foreign Application Priority Data

Sep. 10, 2001 (JP) .............................. 2001-272897

(51) Int. Cl.
*C07D 211/32* (2006.01)
(52) U.S. Cl. ..................................................... 546/225
(58) Field of Classification Search ................. 546/225
See application file for complete search history.

(56) References Cited

FOREIGN PATENT DOCUMENTS

| | | |
|---|---|---|
| JP | 5-59903 | 9/1993 |
| JP | 10-507748 | 7/1998 |
| WO | WO 85/00599 | 2/1985 |
| WO | WO 96/12700 | 5/1996 |

OTHER PUBLICATIONS

*Tetrahedron Letters*, 37, 1996, 6399-402.

*Primary Examiner*—Patricia L. Morris
(74) *Attorney, Agent, or Firm*—Jacobson Holman PLLC

(57) ABSTRACT

A method of manufacturing a pipecolamide derivative, characterized in that pipecolic acid or an acid salt thereof is reacted with an amine in an inert solvent in the presence of a condensing agent such as dicyclohexylcarbodiimide, 1-ethyl-2-(2-dimethylaminopropyl)carbodiimide, methanesulfonyl chloride or phosphoryl chloride. Pipecolamide derivatives, particularly in optically active forms thereof can be efficiently and economically manufactured without harmful gas by-products.

12 Claims, No Drawings

US 7,247,729 B2

METHOD FOR PRODUCING PIPECOLAMIDE DERIVATIVE

This is a nationalization of PCT/JP02/09200 filed Sep. 10, 2002 and published in Japanese.

TECHNICAL FIELD

The present invention relates to a method of manufacturing a pipecolamide derivative, and more particularly, to a manufacturing method suitable for manufacturing an optically active form thereof.

TECHNICAL BACKGROUND

Pipecolamide derivatives, particularly in optically active forms thereof, are useful as an intermediate in the manufacturing of topical anesthetics. For example, L-pipecolic acid-2,6-xylidide is employed as an intermediate in the manufacturing of excellent topical anesthetics, for example, levobupivacaine and ropivacaine.

Numerous approaches have been proposed thus far with regard to methods of manufacturing pipecolamide derivatives, particularly in optically active forms thereof.

For example, (1) Japanese Examined Patent Publication (KOUKOKU) Heisei No. 5-59903 discloses a method of manufacturing pipecolamide derivatives by chloridizing pipecolic acid in advance to obtain pipecolic acid chloride, which is then reacted with an amine; (2) Publication of Japanese Translation of PCT International Application (KOUHYO) Heisei No. 10-507748 discloses a method of manufacturing pipecolamide derivatives in a one-pot by reacting pipecolic acid hydrochloride with thionyl chloride to obtain pipecolic acid chloride, which is then reacted with an amine; and (3) Tetrahedron Lett., 27, 6399-6402 (1996) discloses a method of manufacturing pipecolamide derivatives in a four-step reaction employing a starting material in the form of L-lysine with a protected α-amino group.

However, in manufacturing method (1), acetyl chloride, which is difficult to handle, is employed as a reaction solvent. Further, pipecolic acid chloride must be isolated as an intermediate, rendering the manufacturing process complex and inefficient. Still further, careful attention is required in the handling of the acid chloride, which is highly reactive with water. Although manufacturing method (2) is an efficient one-pot manufacturing method not requiring isolation of pipecolic acid chloride, thionyl chloride is employed as an acid-chloridizing reagent, requiring care for human bodies and the environment with respect to equipments to handle harmful sulfurous acid gas generated during the reaction. Manufacturing method (3) is an industrially unsuitable manufacturing method involving numerous manufacturing steps and a diazonium intermediate presenting a risk of explosion. Therefore, these methods are insufficient.

Accordingly, it is an object of the present invention to provide a method of efficiently manufacturing pipecolamide derivatives, particularly in optically active forms thereof, without harmful gas by-products.

The present inventors conducted extensive research to solve the aforementioned problem. They discovered that it was possible to efficiently produce pipecolamide derivatives without protecting an imino group of pipecolic acid by reacting pipecolic acid with an amine in the presence of a certain type of condensing agent. They further discovered that optically active pipecolamide derivatives could be obtained without a decrease in optical purity during the reaction process when optically active pipecolic acid was employed as a starting material. The present invention was devised based on such knowledge.

DISCLOSURE OF THE INVENTION

That is, the present invention provides a method of manufacturing a pipecolamide derivative, characterized in that pipecolic acid or an acid salt thereof is reacted with an amine in an inert solvent in the presence of a condensing agent.

BEST MODE FOR CARRYING OUT THE INVENTION

In the manufacturing method of the present invention, a starting compound in the form of free pipecolic acid is suspended and dissolved in an inert solvent, and optionally further reacted with hydrogen chloride gas or hydrogen bromide gas—or hydrochloric acid, hydrobromic acid or the like dissolved in the above inert solvent—to prepare a solution of free pipecolic acid or an acid salt thereof. Examples of such inert solvents that are suitable for use are: tetrahydrofuran, diethylether, 1,4-dioxane, hexane, toluene, acetonitrile, benzene, chloroform, dimethylformamide, and dimethyl sulfoxide, with the preference of tetrahydrofuran, 1,4-dioxane, toluene, and acetonitrile.

The solution of free pipecolic acid or the acid salt thus obtained is added and reacted with a condensing agent and then an amine to obtain a pipecolamide derivative in a one-pot reaction process. Examples of condensing agents suitable for use are: dicyclohexylcarbodiimide, 1-ethyl-3-(3'-dimethylaminopropyl)carbodiimide, methanesulfonyl chloride, and phosphoryl chloride, with the preference of methanesulfonyl chloride and phosphoryl chloride. Since these condensing agents do not produce harmful sulfurous acid gas in the reaction process, they are better than thionyl chloride employed in the known methods. In particular, phosphoryl chloride affords a reaction yield that is equal to or greater than that of thionyl chloride and is particularly desirable. When employing methanesulfonyl chloride as a condensing agent, free pipecolic acid may be employed in addition to acid salts thereof. When using other condensing agents mentioned above, an acid salt of pipecolic acid is suitably employed.

Various amines, such as aromatic and aliphatic amines, can be employed. Aromatic amines are employed with preference; examples of which are 2,6-dimethylaniline, 2,4,6-trimethylaniline, and 2-methylaniline.

Specific examples of the pipecolamide derivatives obtained by the manufacturing method of the present invention are: pipecolic acid-2,6-xylidide, pipecolic acid-2-toluidide, pipecolic acid-2,4,6-methidide, and pipecolic acid-2,4-xylidide.

The reaction temperature ranges from −20° C. to 120° C., preferably from 0° C. to 70° C. The reaction time ranges from 1 hour to 96 hours, preferably from 4 hours to 24 hours. The ratio of free pipecolic acid or an acid salt thereof, a condensing agent, and an amine employed ranges from 1:1:1 to 1:20:40, preferably from 1:1:1 to 1:5:10.

In order to purify the pipecolamide derivative thus produced from the reaction mixture, water is first added thereto to decompose the condensing agent remaining in the reaction mixture, and then the product is washed with the aforementioned inert solvent at pH 2 to 7. The product is then extracted using the same solvent at pH 9 to 11 and crystallized, and, as needed, chromatography with silica gel or ion exchange resin is conducted, or recrystallization is conducted, to purify the pipecolamide derivative.

EXAMPLES

Specific examples will be given below to describe the present invention in greater detail; however, the manufacturing method of the present invention is not limited thereto.

Example 1

Synthesis of pipecolic acid-2,6-xylidide (1)

A 100 mg quantity of (free) L-pipecolic acid was suspended in 1 mL of tetrahydrofuran, 62 μL (1.05 equivalents) of methanesulfonyl chloride were added, and the mixture was stirred for 20 min. at 50° C. A 192 μL (2 equivalents) quantity of 2,6-dimethylaniline was added, the mixture was stirred overnight, 62 μL of methanesulfonyl chloride and 192 μL of 2,6-dimethylaniline were similarly added, and the mixture was again stirred overnight. A 2 mL quantity of water was added to the reaction mixture, the aqueous phase was adjusted to pH 4 with 2 mol/L of sodium hydroxide, and the organic phase was discarded. The remaining aqueous phase was then adjusted to pH 7 with 2 mol/L of sodium hydroxide and washed with 2 mL of toluene. Subsequently, the product was adjusted to pH 9 with 2 mol/L of sodium hydroxide and the product of interest was extracted with toluene. The toluene phase was dried with sodium sulfate anhydride, concentrated under reduced pressure, and dried under vacuum, yielding 67 mg (a crude yield of 42%) of crude extract. The purity was estimated about 80% by NMR.

Example 2

Synthesis of pipecolic acid-2,6-xylidide (2)

A 100 mg quantity of (free) L-pipecolic acid was suspended in 1.5 mL (a 15-fold quantity) of toluene, 284 μL (2.0 equivalents) of 4 mol/L hydrochloric acid/dioxane were added, and the mixture was stirred for one hour. Subsequently, 145 μL (2.0 equivalents) of phosphoryl chloride were added. A 282 μL (3.0 equivalents) quantity of 2,6-dimethylaniline was then gradually added and the mixture was stirred overnight at room temperature. 10 mL of water was added to the reaction solution and the mixture was adjusted to pH 6 with 2 mol/L of sodium hydroxide. The mixture was washed twice with 10 mL of toluene. The aqueous phase was further adjusted to pH 11 and extracted twice with 10 mL of toluene. The organic phase was dried with sodium sulfate anhydride, filtered, and evaporated under reduced pressure, yielding 108 mg (60% yield) of pipecolic acid-2,6-xylidide.

Reference Example 1

Synthesis of Levobupivacaine Hydrochloride

A 1.5 g quantity of pipecolic acid-2,6-xylidide was dissolved in 7.5 mL of dimethylformamide, 1.45 g of potassium carbonate and 1.1 mL of butyl bromide were added, and the mixture was stirred for two hours at 80° C. The reaction solution was returned to room temperature and then filtered. The filtrate obtained was gradually added dropwise to 45 mL of water while cooling on ice. The mixture was filtered and evaporated under reduced pressure, yielding 1.62 g (87% yield) of a pale yellow solid. This solid was dissolved in 2.2 mL of isopropanol, after which 1.8 mL of 4 mol/L hydrochloric acid/dioxane were added dropwise with stirring. The mixture was stirred for 20 min. at 0° C. and filtered, yielding 1.28 g (70% yield) of levobupivacaine hydrochloride.

INDUSTRIAL APPLICABILITY

The method of the present invention is characterized in that, by employing an optically active form of pipecolic acid as a starting material, the corresponding optically active pipecolamide derivative can be obtained with high yield without a decrease of optical purity. Therefore, according to the method of the present invention, optically active pipecolamide derivatives such as the L-pipecolic acid-2,6-xylidide, that are employed as an intermediate in the manufacturing of topical anesthetics such as levobupivacaine and ropivacaine, can be economically manufactured employing, as a starting material, L-pipecolic acid that can be manufactured in a large scale by fermentation.

The invention claimed is:

1. A method of manufacturing a topical anesthetic intermediate comprising reacting
   a) free pipecolic acid or an acid salt thereof
   b) with an aromatic amine
   c) in an inert solvent
   d) in the presence of a condensing agent, wherein the condensing agent is dicyclohexylcarbodiimide, 1-ethyl-3-(3'-dimethylaminopropyl)carbodiimide, methanesulfonyl chloride, or phosphoryl chloride,
to produce a topical anesthetic intermediate selected from the group consisting of pipecolic acid-2,6-xylidide, pipecolic acid-2-toluidide, pipecolic acid-2,4,6-methidide, and pipecolic acid-2,4-xylidide.

2. The method of manufacturing according to claim 1, wherein the aromatic amine is 2,6-dimethylaniline, 2,4,6-trimethylaniline, or 2-methylaniline.

3. The method of manufacturing according to claim 1, wherein the topical anesthetic intermediate is pipecolic acid-2,6-xylidide.

4. The method of manufacturing according to claim 1, wherein the topical anesthetic intermediate is pipecolic acid-2-toluidide.

5. The method of manufacturing according to claim 1, wherein the topical anesthetic intermediate is pipecolic acid-2,4,6-methidide.

6. The method of manufacturing according to claim 1, wherein the topical anesthetic intermediate is pipecolic acid-2,4-xylidide.

7. The method of manufacturing according to claim 1, wherein the free pipecolic acid or acid salt thereof is L-pipecolic acid or acid salt thereof.

8. The method of manufacturing according to claim 2, wherein the free pipecolic acid or acid salt thereof is L-pipecolic acid or acid salt thereof.

9. The method of manufacturing according to claim 3, wherein the free pipecolic acid or acid salt thereof is L-pipecolic acid or acid salt thereof.

10. The method of manufacturing according to claim 4, wherein the free pipecolic acid or acid salt thereof is L-pipecolic acid or acid salt thereof.

11. The method of manufacturing according to claim 5, wherein the free pipecolic acid or acid salt thereof is L-pipecolic acid or acid salt thereof.

12. The method of manufacturing according to claim 6, wherein the free pipecolic acid or acid salt thereof is L-pipecolic acid or acid salt thereof.

* * * * *